US00PP08546P

United States Patent [19]

Zaiger et al.

[11] Patent Number: Plant 8,546

[45] Date of Patent: Jan. 18, 1994

[54] INTERSPECIFIC TREE "FLAVORICH"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 35,174

[22] Filed: Mar. 22, 1993

[51] Int. Cl.[5] ..... A01H 5/00

[52] U.S. Cl. ..... Plt./38.1

[58] Field of Search ..... Plt. 38.1

*Primary Examiner*—James R. Feyrer

[57] ABSTRACT

A new and distinct variety of interspecific tree (Plum×(Plum×Plum Cot)) which has the unique combination of features that are desirable in a new variety.

1. Heavy and regular production of large fruit.
2. Fruit with excellent flavor and eating quality.
3. Fruit with firm flesh, good handling and shipping quality.
4. Large tree size with vigorous upright growth.
5. Fruit ripening in the late maturity season.
6. Fruit holding firm on the tree 15 to 20 days after shipping ripe.
7. Fruit with high soluble solids (brix) averaging approximately 20 degrees with the refractometer.
8. Fruit with an attractive dark violet to blackish blue skin color.

1 Drawing Sheet

ORIGIN OF THE VARIETY

The present new and distinct variety of interspecific tree was developed by us in our experimental orchard located near Modesto, Calif., as a cross between Friar Plum (non-patented) and a selected seedling with the field identification number 27EB180. The seedling number 27EB180 originated from a cross between the selected seedling 60G866 and a plum cot of unknown parentage. The seedling numbered 60G866 originated from a cross between Autumn Rose Plum (non-patented) and Queen Ann Plum (non-patented). The new variety was selected from a large group of seedlings which were grown and maintained by us, one such seedling, which is the present variety, exhibited especially desirable fruit characteristics and was selected for asexual reproduction and commercialization.

ASEXUAL REPRODUCTION OF THE VARIETY

The present new variety of interspecific tree was asexually propagated by budding, as performed by us in our experimental orchard located near Modesto, Calif. and shows that all characteristics of the tree and its fruit are established and transmitted through succeeding propagations and comes true to the original tree in all respects.

SUMMARY OF THE VARIETY

The new and distinct variety of interspecific tree is of large size, vigorous upright growth and a productive and regular bearer of large, clingstone fruit with excellent flavor and eating quality. Characterized as to its novelty by its firm flesh, its good handling and shipping quality, its ability to hold firm on the tree 15 to 20 days after shipping ripe, its high soluble solids (brix) approximately 20 degrees and ripening in the late maturity season, approximately 7 weeks after Friar Plum (non-patented).

DESCRIPTION OF THE PHOTOGRAPHS

The accompanying color photographic illustrations show a small branch with the foliage attached and fruit of the present interspecific variety.

The upper surface of the leaves are shown with an exterior and sectional view of the fruit being divided in the suture plane to show flesh coloration, pit cavity and a stone remaining in place.

The photographic illustrations were taken shortly after being picked at maturity (firm ripe) and the colors are as nearly true as is reasonably possible in a color representation of this type.

DESCRIPTION OF THE VARIETY

The following is a detailed botanical description of the new and distinct variety of interspecific tree, its flowers, foliage and fruit as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Bearer.*—Regular.
- *Production.*—Productive.

Trunk:
- *Size.*—Large.
- *Texture.*—Medium shaggy.
- *Color.*—Grayish brown to brown. (5-E-3) to (5-E-5).

Branches:
- *Size.*—Medium.
- *Texture.*—Smooth to medium rough.
- *Lenticels.*—Medium number. Small Size.
- *Color.*—Brown to reddish brown.

Leaves:
- *Size.*—Large. Average length — 4¼" to 5". Average width — 1½" to 1⅞".
- *Surface.*—Smooth.
- *Form.*—Oblanceolate.
- *Margin.*—Serrate.
- *Thickness.*—Medium to thick.

*Petiole.*—Medium length. Thick, grooved on the upper surface.

*Glands.*—Globose. Number varies from 1 to 3. Average number 2. Small to medium size. Located on base of leaf blade and upper portion of petiole.

*Color.*—Upper surface — green to dark green (27-E-8) to (27-F-8). Lower surface — grayish green to green (27-E-5) to (27-E-7).

Flower buds:

*Size.*—Medium.

*Form.*—Plump.

*Length.*—Medium.

Flowers:

*Size.*—Medium.

*Blooming period.*—Mar. 2, 1991 to Mar. 9, 1991. Varies slightly with climatic conditions.

*Pollen.*—Present.

*Color.*—White.

Fruit:

*Maturity when described.*—Firm ripe.

*Date of first picking.*—Sep. 15, 1991.

*Date of last picking.*—Sep. 20, 1991.

*Size.*—Large. Average diameter axially — 2¼" to 2½". Average transversely in suture plane — 2⅝" to 3".

*Form.*—Nearly Globose — slightly flattened at base and apex.

*Suture.*—Shallow — extends from base to apex.

*Ventral surface.*—Rounded — nearly smooth.

*Apex.*—Slightly retuse — varies from flat to slight depression.

*Base.*—Retuse.

*Cavity.*—Rounded — slightly elongated in suture plane Average depth — ½". Average breadth — ⅝".

Flesh:

*Ripens.*—Evenly.

*Texture.*—Firm — meaty.

*Flavor.*—Excellent, good balance between acid and sugar.

*Fibers.*—Small, tender.

*Juice.*—Moderate.

*Aroma.*—Slight.

*Eating quality.*—Excellent.

*Color.*—Dark yellow to light orange (6-A-4) to (6-B-6). Pit cavity reddish brown(8-D-8) to (8-E-8) surface stained by stone color.

Skin:

*Thickness.*—Medium.

*Texture.*—Medium, tenacious to flesh.

*Down.*—Wanting.

*Bloom.*—Moderate.

*Tendency to crack.*—None.

*Color.*—Deep magenta to dark blue ground color (14-F-7) to (14-F-8) overspread with dark violet to blackish blue (18-F-8) to (19-F-8).

Stone:

*Type.*—Clingstone.

*Size.*—Medium. Average length — 1". Average breadth — ¾". Average thickness — ⅝".

*Form.*—Ovoid.

*Sides.*—Equal to unequal.

*Base.*—Usually straight — varies from straight to slightly rounded.

*Surface.*—Slightly pitted throughout.

*Ridges.*—Very small ridges on both sides of suture plane.

*Tendency to split.*—None.

*Apex.*—Acuminate.

*Color.*—Light brown to reddish brown (8-D-6) to (8-D-8).

Use: Dessert.

*Market.*—Local and long distance.

Keeping quality: Good.

Shipping quality: Good.

The interspecific tree, its flowers, foliage and fruit herein described, may vary in slight detail due to climatic, soil conditions and cultural practices under which the variety may be grown; the present botanical description is that of the variety grown under the ecological conditions prevailing near Modesto, Calif.

We claim:

1. A new and distinct variety of interspecific tree, substantially as illustrated and described, characterized by its large size, vigorous, upright growth and a productive and regular bearer of large, firm, clingstone fruit with good handling and shipping quality; the fruit is further characterized by having high soluble solids (brix) averaging 20 degrees on the refractometer, having excellent flavor and eating quality, holding firm on the tree for 15 to 20 days after shipping ripe and ripening in the late maturity season approximately 7 weeks after Friar Plum (non-patented).

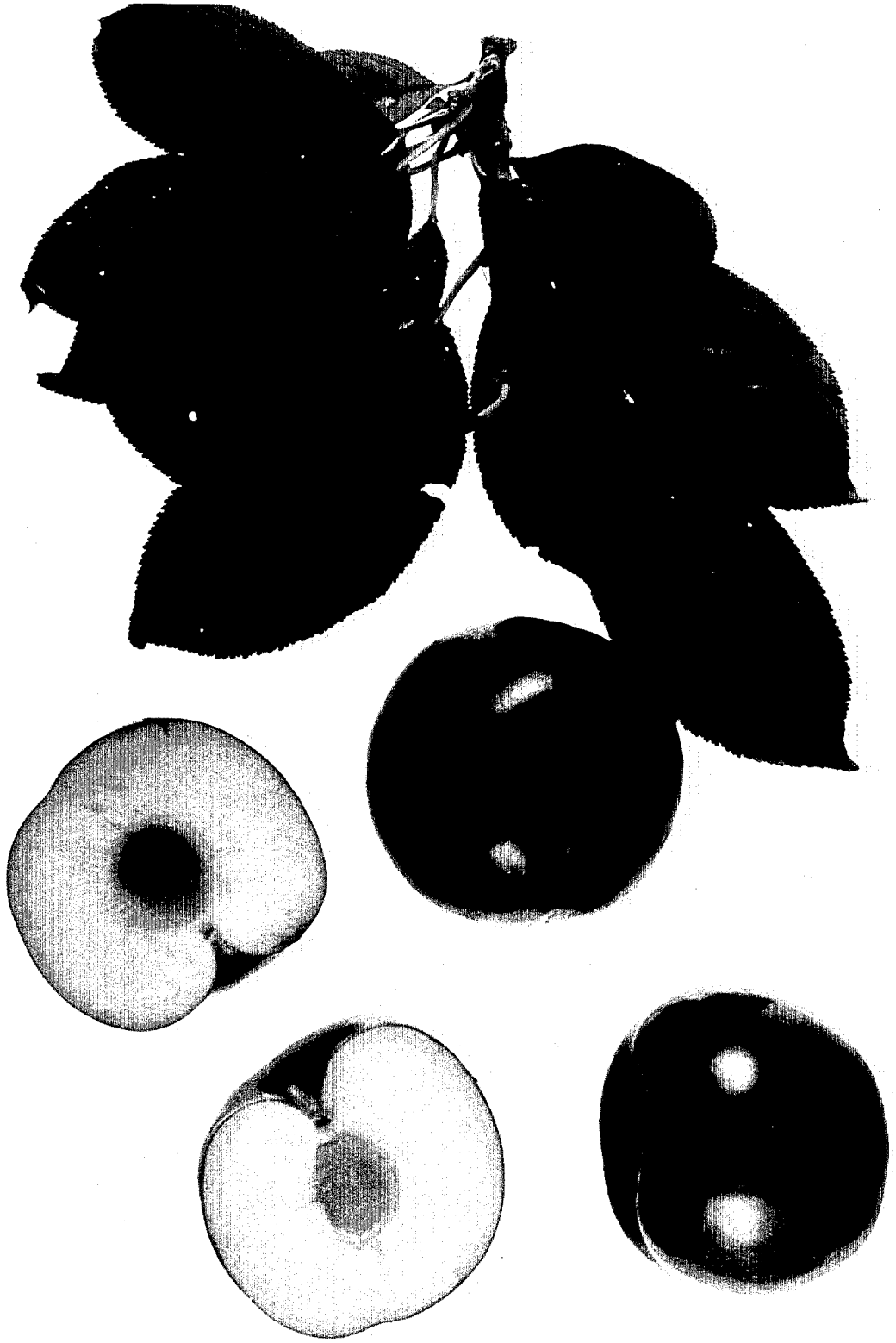

* * * * *